United States Patent [19]

Ogata et al.

[11] Patent Number: 5,112,906
[45] Date of Patent: May 12, 1992

[54] ORGANIC NONLINEAR OPTICAL MATERIAL

[75] Inventors: Naoya Ogata, 29-6, Asagayakita 6-chome, Suginami-ku, Tokyo; Yasuhiko Yokowo, Ichihara, both of Japan

[73] Assignees: Naoya Ogata; Seizo Miyata, both of Tokyo; Ube Industries Ltd., Yamaguchi; Research Development Corporation of Japan, Tokyo, all of Japan

[21] Appl. No.: 504,921

[22] Filed: Apr. 5, 1990

[30] Foreign Application Priority Data

Apr. 28, 1989 [JP] Japan .................................. 1-110127

[51] Int. Cl.$^5$ .................................................. C08F 8/00
[52] U.S. Cl. ........................................ 525/61; 525/60; 359/240; 359/326; 385/122
[58] Field of Search ................................. 525/61, 60

[56] References Cited

U.S. PATENT DOCUMENTS

| | | | |
|---|---|---|---|
| 3,821,167 | 6/1974 | Asano | 525/61 X |
| 3,943,150 | 3/1976 | Kashkina et al. | 525/61 X |
| 4,762,912 | 8/1988 | Leslie et al. | 252/299.01 X |
| 4,818,802 | 4/1989 | Choe | 525/329.7 X |
| 4,867,538 | 9/1989 | Yoon et al. | 350/350 R |

Primary Examiner—Joseph L. Schofer
Assistant Examiner—J. M. Reddick
Attorney, Agent, or Firm—Frishauf, Holtz, Goodman & Woodward

[57] ABSTRACT

Disclosed are an organic nonlinear optical material comprising a 4-nitrophenylaminoacetaldehyde acetal represented by the following general formula:

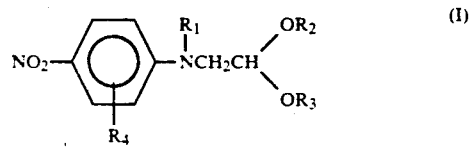

and a polymeric organic nonlinear optical material comprising an acetalized polyvinyl alcohol having the above-mentioned 4-nitrophenylaminoacetaldehyde acetal as the side chain.

1 Claim, No Drawings

ORGANIC NONLINEAR OPTICAL MATERIAL

BACKGROUND OF THE INVENTION

(1) Field of the Invention

The present invention relates to an organic nonlinear optical material. More particularly, the present invention relates to a novel organic nonlinear optical material comprising a 4-nitrophenylaminoacetaldehyde acetal, and also to a novel organic nonlinear optical material comprising an acetalized polyvinyl alcohol having the above-mentioned substance as the side chain.

(2) Description of the Prior Art

Since an organic nonlinear optical material has a large nonlinearity, it is expected that this material will be used as a base material of an optoelectronic device in the future.

For example, urea, 2-methyl-4-nitroaniline, 4-nitro-4'-methylbenzylideneaniline and 3-methyl-4-nitropyridine N-oxide are known as typical instances of the organic nonlinear optical material.

However, when these organic nonlinear optical materials are used as optical elements, the following serious problems should be solved.

(1) Most of the materials of the 4-nitroaniline series have a subliming property and have no dimensional stability.

(2) When a semiconductor laser is used as the light source, a nonlinear organic material should be used as an optical waveguide. The above-mentioned organic materials are, however, poor in the moldability and processability for the production of optical waveguides.

Furthermore, the above-mentioned organic materials involve a problem concerning electric field orientation.

SUMMARY OF THE INVENTION

It is an object of the present invention to provide an organic nonlinear optical material having an acetal group capable of reacting with polyvinyl alcohol, an organic nonlinear optical material having this substance as the side chain, and an organic nonlinear optical material excellent in electric field orientation, which comprises an acetalized polyvinyl alcohol having this substance as the side chain.

In accordance with one aspect of the present invention, there is provided an organic nonlinear organic material comprising a 4-nitrophenylaminoacetaldehyde acetal represented by the following general formula(I):

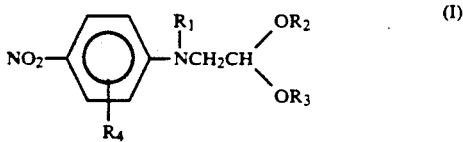

wherein $R_1$, $R_2$ and $R_3$ represent each a hydrogen atom, or a linear or branched alkyl group having 1 to 6 carbon atoms, and $R_4$ represents a hydrogen atom, a linear or branched alkyl group having 1 to 6 carbon atoms, a linear or branched alkoxy group having 1 to 6 carbon atoms, a hydroxyl group, a nitro group, or a halogen atom.

In accordance with another aspect of the present invention, there is provided a polymeric organic nonlinear optical material comprising an acetalized polyvinyl alcohol represented by the following general formula (II):

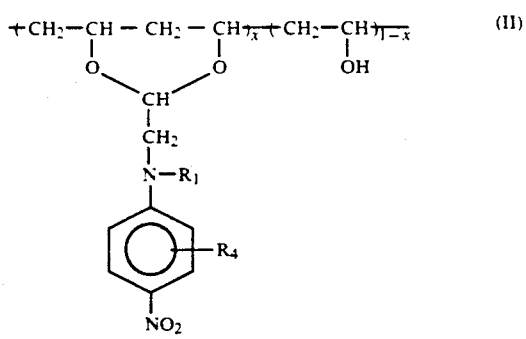

wherein $R_1$ represents a hydrogen atom, or a linear or branched alkyl group having 1 to 6 carbon atoms, $R_4$ represents a hydrogen atom, a linear or branched alkyl group having 1 to 6 carbon atoms, a linear or branched alkoxy group having 1 to 6 carbon atoms, a hydroxyl group, a nitro group, or a halogen atom, and x is a number of $0 < x < 1$.

The organic nonlinear optical material of the present invention has an excellent electric field orientation.

DETAILED DESCRIPTION OF THE INVENTION

In the general formula (I), $R_2$ and $R_3$ may together form a cyclic structure such as an ethylene structure. The 4-nitrophenylaminoacetaldehyde acetal represented by the general formula (I) can be used in this form or in the form of a salt with an inorganic acid or organic acid.

The 4-nitrophenylaminoacetaldehyde acetal of the present invention can be synthesized according to various processes. One example will now be described.

Namely, the intended compound can be prepared by reacting a 4-nitrofluorobenzene derivative with aminoacetal in the presence of a base. Any of solvents capable of dissolving the starting compounds therein can be used as the reaction solvent. For example, there can be mentioned benzene, toluene, xylene, DMSO, DMF, NMP, chloroform, methylene chloride, ethyl alcohol, metyl alcohol, ether, THF, hexane and cyclohexane. When the starting materials are liquid, the reaction can be carried out in the absence of any solvent. As the base used for the reaction, there can be mentioned carbonates such as sodium carbonate, potassium carbonate, lithium carbonate, magnesium carbonate and calcium carbonate, and hydrogencarbonates such as sodium hydrogenecarbonate and potassium hydrogencarbonate. These bases may be anhydrous or contain water of crystallization. As the organic base, there can be used pyridine, pyrimidine, piperazine, triazine, lutidine, morpholine and pyrrolidine. These bases are added so that the acetal group is not decomposed into an aldehyde by hydrofluoric acid formed by the reaction.

The reaction is conducted at room temperature or under heating, and the reaction temperature depends on the kinds of the starting materials used. Aminoacetal is used for the reaction in an amount of 1 to 5 moles, preferably 1 to 2 moles, per mole of the 4-nitrofluorobenzene.

The acetalized polyvinyl alcohol of general formula (II) used in the present invention is synthesized by reacting the 4-nitrophenylaminoacetaldehyde acetal represented by general formula (I) with polyvinyl alcohol. An example of the synthesis process will now be described.

Polyvinyl alcohol is dissolved in an appropriate solvent, and the starting acetal is added to the solution in an amount of 1 to 5 moles, preferably 2 to 3 moles, per mole of the polyvinyl alcohol and an acid is further added in an amount equimolar to the acetal. The mixture is heated and stirred, and the precipitated polymer is purified by reprecipitation or the like to obtain an acetalized polyvinyl alcohol.

The kind of the polyvinyl alcohol is not particularly critical, so far as the degree of polymerization is 500 to 2400. Namely, any of stereoregular polyvinyl alcohol, random polyvinyl alcohol, isotactic polyvinyl alcohol, heterotactic polyvinyl alcohol and syndiotactic polyvinyl alcohol can be used.

Any of solvents capable of dissolving polyvinyl alcohol therein can be used as the solvent, but water is preferably used. As the acid to be added, there can be mentioned hydrochloric acid, sulfuric acid, acetic acid and p-toluenesulfonic acid. The acid is added in an amount of 1 to 5 moles, preferably 1 to 2 moles, per mole of the starting acetal. The reaction is carried out under heating with stirring at a temperature of 0 to 100° C., preferably 50 to 80° C.

The molar proportion x of the acetal in the acetalized polyvinyl alcohol can be controlled by the molar ratio of the starting materials and the reaction temperature. In order to use the obtained product as a nonlinear optical material, it is necessary that many molecules having a nonlinear function should be introduced into polyvinyl alcohol through acetal bonds. In view of the hardness and glass transition point of the film, the amount of the hydroxyl group and the physical properties, it is preferred that the molar proportion x of the acetal be 0.3 to 0.9.

In the present invention, the 4-nitrophenylaminoacetaldehyde of general formula (I) or the acetalized polyvinyl alcohol of general formula (II) can be used singly as the organic nonlinear optical material, or used in the form of a mixture with other polymer matrix. A polymer matrix having a reduced light damage is preferably used. As the polymer matrix, there can be mentioned, for example, poly-ε-caprolactone, polyesters such as polybutylene sebacate and polyhexamethylene adipate, polyethylene oxide, polymethacrylate, nylon, cellulose, epoxy resins, phenol-novolak resins, cresol-novolak resins and aniline-novolak resins.

When the obtained nonlinear optical polymer is oriented in an electric field or magnetic field, a second harmonic (SHG) is generated. In case of the orientation in an electric field, in general, such a high voltage as 200 kV/cm should be applied.

In case of the nonlinear optical polymer of the present invention, at such a relatively low voltage as 30 kV/cm the orientation is effected in the direction of the electric field, and the nonlinear optical polymer of the present invention is practically valuable in that the orientation treatment can be performed relatively easily.

Furthermore, the polymer of the present invention can be oriented by utilizing the hydrophilic property of the residual hydroxyl group of polyvinyl alcohol, that is, by developing the polymer as a monomolecular film (LB film) on the water surface and scooping up the film on a substrate.

The present invention will now be described in detail with reference to the following Examples.

EXAMPLE 1

To 5.05 g (0.048 mole) of aminoacetaldehyde dimethylacetal were added 5.64 g (0.040 mole) of p-fluoronitrobenzene, 4.03 g (0.048 mole) of sodium hydrogencarbonate and 5 ml of dimethyl sulfoxide and reaction was carried out at 80° C. for 12 hours. After the reaction, the reaction mixture was poured into 100 ml of water to precipitate a yellow solid. The solid was dissolved in 150 ml of benzene, and the solution was washed with a liquid mixture comprising 50 ml of water and 1 ml of hydrochloric acid and with 50 ml of water two times. The residual benzene layer was dried with anhydrous sodium carbonate. After the drying, the benzene layer was concentrated and the obtained yellow solid was washed with hexane and dried under reduced pressure to obtain 8.65 g (the yield was 95.6%) of a crystal of 4-nitrophenylaminoacetaldehyde dimethyl acetal.

The physical property values of the obtained product are as follows.

MS spectrum (EI-MS measurement): m/e=226 ($M^+$), 195, 151, 117, 105, 75

IR spectrum (KBr tablet method), $cm^{-1}$: 3340, 2910, 1590, 1300, 1100

The SHG value was determined in the following manner.

Namely, 4-nitrophenylaminoacetaldehyde dimethyl acetal was held between slide glass sheets, and the sample was irradiated with pulses of 10 ns by an Nd-YAG laser (1064 nm) having a Q switch. SHG generated from the sample was detected.

Urea was used as the reference sample. SHG stronger than that of urea was confirmed.

EXAMPLE 2

In 35 ml of water was dissolved 0.5 g of polyvinyl alcohol having a polymerization degree of 1500 at 50° C., and 2.1 ml of hydrochloric acid was added to the solution. Then, 5.99 g (0.0249 mole) of 4-nitrophenylmethylaminoacetaldehyde dimethyl acetal and 20 ml of methyl alcohol were added to the solution, and the mixture was heated with stirring at 50° C. for 12 hours. The formed tar-like solid was dissolved in 25 ml of dimethylformamide at 60° C. and the solution was poured into 100 ml of acetonitrile to effect precipitation. By repeating this precipitation two times, 1.32 g of the intended acetalized polyvinyl alcohol was obtained.

The acetalized polyvinyl alcohol was dissolved in dimethylformamide at a concentration of 10% by weight, and the solution was spin-coated on a glass sheet having an ITO electrode vacuum-deposited thereon and an electric field of 30 kV/cm was applied at 80° C. for 1 hour. When the measurement was carried out in the same manner as described in Example 1, SHG could be observed. When the intensity of SHG in the direction of the electric field was compared with the intensity of SHG in the direction rectangular to the direction of the electric field by polarizing laser beams, it was found that the intensity ratio was about 70:1 and the sample was oriented substantially completely in the direction of the electric field.

We claim:

1. A polymeric organic nonlinear optical material comprising an acetalized polyvinyl alcohol represented by the following general formula (II):

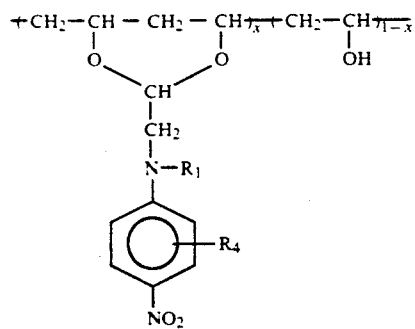
wherein $R_1$ represents a hydrogen atom, or a linear or branched alkyl group having 1 to 6 carbon atoms, $R_4$ represents a hydrogen atom, a linear or branched alkyl group having 1 to 6 carbon atoms, a linear or branched alkoxy group having 1 to 6 carbon atoms, a hydroxyl group, a nitro group, or a halogen atom, and x is a number of $0 < x < 1$.
* * * * *